United States Patent
Cai et al.

(10) Patent No.: US 10,800,810 B2
(45) Date of Patent: Oct. 13, 2020

(54) ACTIVE PEPTIDE FOR INHIBITING AMPA RECEPTOR AND PREPARATION METHOD AND USE THEREOF

(71) Applicant: CHINA NATIONAL RESEARCH INSTITUTE OF FOOD AND FERMENTATION INDUSTRIES, Beijing (CN)

(72) Inventors: Muyi Cai, Beijing (CN); Huaiyu Gu, Beijing (CN); Jun Lu, Beijing (CN); Xingchang Pan, Beijing (CN); Yong Ma, Beijing (CN); Liang Chen, Beijing (CN)

(73) Assignee: CHINA NATIONAL RESEARCH INSTITUTE OF FOOD AND FERMENTATION INDUSTRIES, Beijing (CN)

( * ) Notice: Subject to any disclaimer, the term of this patent is extended or adjusted under 35 U.S.C. 154(b) by 0 days.

(21) Appl. No.: 15/834,026

(22) Filed: Dec. 6, 2017

(65) Prior Publication Data
US 2018/0094028 A1 Apr. 5, 2018

Related U.S. Application Data

(63) Continuation of application No. PCT/CN2015/083571, filed on Jul. 8, 2015.

(51) Int. Cl.
| C07K 1/12 | (2006.01) |
| C07K 1/14 | (2006.01) |
| C07K 1/36 | (2006.01) |
| C07K 5/113 | (2006.01) |
| C07K 1/34 | (2006.01) |
| C12P 21/06 | (2006.01) |
| A61K 38/00 | (2006.01) |

(52) U.S. Cl.
CPC .............. *C07K 5/1021* (2013.01); *C07K 1/12* (2013.01); *C07K 1/14* (2013.01); *C07K 1/34* (2013.01); *C07K 1/36* (2013.01); *C12P 21/06* (2013.01); *C12Y 304/22002* (2013.01); *A61K 38/00* (2013.01)

(58) Field of Classification Search
None
See application file for complete search history.

(56) References Cited

U.S. PATENT DOCUMENTS

2009/0105159 A1    4/2009   Hitzl et al.

FOREIGN PATENT DOCUMENTS

| CN | 1382806 A | | 12/2002 |
| CN | 1738618 A | | 2/2006 |
| CN | 1781933 A | * | 6/2006 |
| CN | 1781933 A | | 6/2006 |
| CN | 101061827 A | | 10/2007 |
| CN | 101240312 A | | 8/2008 |
| CN | 103205480 A | | 7/2013 |
| CN | 103238870 A | | 8/2013 |
| CN | 104694615 A | | 6/2015 |
| JP | 2001200000 A | | 7/2001 |
| JP | 2005-053798 A | | 3/2005 |
| JP | 2005-0314265 A | | 11/2005 |
| JP | 2007-039394 A | | 2/2007 |
| JP | 2009-0658734 A | | 4/2009 |
| WO | 2014/096090 A1 | | 6/2014 |

OTHER PUBLICATIONS

International Search Report of corresponding International PCT Application No. PCT/CN2015/083571, dated Apr. 15, 2016.

* cited by examiner

*Primary Examiner* — Kevin S Orwig
(74) *Attorney, Agent, or Firm* — J.C. Patents

(57) ABSTRACT

Provided is an active peptide for inhibiting an AMPA receptor and a preparation method and use thereof. The method for preparing the active peptide comprises the following steps: 1) soaking a salmon skin and crushing, adding water and beating, and then adjusting pH to 6.5-7.5; 2) subjecting to a first enzymolysis using a neutral protease; 3) subjecting to a second enzymolysis using papain enzyme and then inactivating enzyme; and 4) centrifuging the enzymatic hydrolysate, and then subjecting the centrifuged supernatant to membrane filtration, concentration and decoloration, to prepare the active peptide. The active peptide contains a tetrapeptide with an amino-acid sequence of Glu-Gly-Ala-Arg. The tetrapeptide has good solubility, can selectively inhibit neuronal synaptic transmission caused by an AMPA receptor, and has a significant antiepileptic effect.

7 Claims, 17 Drawing Sheets

Specification includes a Sequence Listing.

ACTIVE PEPTIDE FOR INHIBITING AMPA RECEPTOR AND PREPARATION METHOD AND USE THEREOF

CROSS-REFERENCE TO RELATED APPLICATIONS

This application is a continuation of International Application No. PCT/CN2015/083571, filed on Jul. 8, 2015, the disclosure of which is hereby incorporated by reference in its entirety.

FIELD OF THE TECHNOLOGY

The present application relates to an active peptide, in particular to an active peptide for inhibiting an AMPA receptor and preparation method and use thereof.

BACKGROUND

Epilepsy is a chronic disease of transitory cerebral dysfunction caused by sudden abnormal electric discharge of cerebral neuron, the main symptom is repeated and uncontrollable spasm. It has become the second most common disease next to headache in the neurology department in China, and about 1-2% of people around the world suffer from this disease. Although more than 15 kinds of antiepileptic drugs are provided by most countries, 20-30% epilepsy patients still cannot efficiently control spasm during attack.

At present, many studies on epilepsy is aimed at finding a more safe and effective drug for inhibiting neuronal excitation, which plays a key role in adjusting neuronal activity of central nervous system of mammalian animals under a physiological and pathological state, especially in adjusting excitation transferring activity that alpha-amino-3-hydroxy-5-methyl-4-isoxazole propionic acid receptor (an AMPA receptor, AMPAR) participates. It has been demonstrated that over excitation of AMPA receptor is the main reason for concentration of intracellular calcium ions being too high, and both intraperitoneal injection of AMPA and encephalocoele injection of AMPA could cause animal model spasm, which indicates the effect of AMPA in production of spasm. Therefore AMPA receptor is an ideal drug target.

Available data show that AMPA receptor inhibitor may have an effect of preventing or treating epilepsy, and a drug that inhibits or attenuates AMPA receptor can inhibit over excitation of neuron so as to protect neuron and inhibit spasm. Typical AMPA receptor competitive inhibitor 2,3-dihydroxy-6-nitro-7-sulfamoyl benzo [f] quinoxaline (NBQX) can play a role in pentylenetetrazole (PTZ) model, but it has low solubility, and may be precipitated in kidney. Although solubility of NBQX derivatives with polar component joined is increased, its ability to penetrate bloodbrain barrier is decreased. Therefore, developing a safe and effective AMPA receptor inhibitor with good solubility as the antiepileptic drug has become an urgent problem to be solved.

SUMMARY

The present application provides an active peptide for inhibiting an AMPA receptor and preparation method and use thereof. The active peptide is of good solubility and safety, and can selectively inhibit neuronal synaptic transmission caused by an AMPA receptor, and has a significant antiepileptic effect.

A first aspect of the present application provides a method for preparing an active peptide, including the following steps:

1) soaking a salmon skin and crushing, adding water and beating, and then adjusting pH to 6.5-7.5, to obtain a slurry;

2) subjecting the slurry to a first enzymolysis by using a neutral protease, to obtain a first enzymatic hydrolysate;

3) subjecting the first enzymatic hydrolysate to a second enzymolysis by using papain enzyme and then inactivating the enzyme, to obtain a second enzymatic hydrolysate; and 4) centrifuging the second enzymatic hydrolysate, and then subjecting the centrifuged supernatant to membrane filtration, concentration and decoloration, to prepare the active peptide.

The active peptide contains a tetrapeptide with an amino-acid sequence of SEQ ID No.17 (abbreviated as EGA).

In the present application, an alkaline solution with a mass content of 0.1-0.5% can be used to soak the salmon skin, which is mainly used to remove fishy smell. During soaking, a mass/volume ratio of the salmon skin to the alkaline solution can be controlled to 1:(2-4), that is, 1 kg of salmon skin is soaked by using 2-4 L of alkaline solution. When the slurry has a too high concentration (the mass/volume ratio>1:2), it has poor fluidity and low enzymolysis efficiency, and when the slurry has a too low concentration (the mass volume ratio<1:4), it has a large subsequent processing volume, and thus the cost accordingly increases. In addition, soaking time can be 5-20 h. The present application does not strictly restrict the alkaline solution used for soaking. In one embodiment, NaOH solution with a mass content of 0.2% can be used to soak the salmon skin, and the mass/volume ratio of the salmon skin to NaOH solution can be 1:3, and the soaking time can be 12 h.

Further, when conducting the first enzymolysis and the second enzymolysis, the amount of the neutral protease can be controlled to 50~500 U/g, the amount of the papain can be controlled to 100~1000 U/g. The amounts of the above two enzymes are based on weight of the salmon skin, and an amount ratio of the neutral protease and the papain can be 1:(1-3). Enzymolysis of the slurry produced from the salmon skin is proceed by using the neutral protease and papain successively, which facilitates degradation of macro-molecular protein into micro-molecular polypeptide, in particular dipeptide to hexapeptide, and thereby improves solubility and absorbability of the active peptide.

Furthermore, it can be controlled that a temperature of the first enzymolysis is 30~60° C., time of the first enzymolysis is 4~6 h, and a temperature of the second enzymolysis is 30~60° C., and time of the second enzymolysis is 1~3 h. If the time of the first enzymolysis and second enzymolysis is too short, it is unfavorable for full degradation of protein, and if the time is too long, it may cause production of unfavorable substances (such as substances with bitter taste and acerb taste). Therefore the above-mentioned enzymolysis time is advisable. The enzyme can be inactivated by conventional method in the art, for example, the enzyme can be inactivated for 10~20 minutes at a temperature of 100~120° C.

Furthermore, rotating speed of the centrifugation in step 4) can be controlled to 2000~6000 r/min, and the centrifugation can be carried out by using a conventional equipment, such as horizontal screw centrifuge, tube centrifuge and so on. The membrane filtration can be proceeded with a ceramic membrane with a pore diameter of 50~1000 nm.

During the membrane filtration, it can be controlled that absolute pressure of the membrane filtration is 0.2~0.4 MPa, and the temperature is 30~80° C. The membrane filtration can further intercept components with larger molecular weight in enzymolysis products, and thereby ensures the solubility and absorbability of the active peptide.

In the present application, the concentrating can be carried out by using a conventional method. For example, a double-effect falling film evaporator is used to carry out evaporation and concentration, and it can be controlled that vapor pressure of the evaporation and concentration is 0.1±0.02 MPa, evaporation temperature is 40~80° C., and concentration of the concentrated solution is 25-30 Baume. Furthermore, the decoloration can be carried out by using a conventional decolorizer, the decolorizer, for example, can be an activated carbon powder. A mass ratio of the decolorizer and filtrate of the concentrated solution can be (10~30):100, the temperature of the decoloration can be controlled at 40~70° C., such as 55° C., and the time of the decoloration can be 30~90 min, and the decoloration can be carried out under agitation. After decoloration, the decolorizer can be removed by a conventional manner, for example, filtering, such as plate-frame filtering. Further, the decoloration can be followed by sterilization and desiccation, and then the active peptide is produced. The desiccation can be for example spray drying.

Further, the method for preparing an active peptide provided in the present application also can include: separating and purifying the active peptide by using a reversed phase high performance liquid chromatography, to obtain the tetrapeptide with an amino acid sequence of SEQ ID No.17.

A second aspect of the present application provides an active peptide, which is produced according to any one of the above described preparation method.

Further, in the active peptide of the present application, the mass content of the peptide with a molecular weight of less than 1000 Da is more than 80%. In addition, the active peptide also includes one or more of polypeptides below: WYN, SEQ ID No.1, SEQ ID No.2, SEQ ID No.3, SEQ ID No.4, QK, SEQ ID No.5, NK, NPR, TQ, RGF, SEQ ID No.6, SR, SEQ ID No.7, SEQ ID No.8, SEQ ID No.9, GR, SSP, KR, AK, GGH, SEQ ID No.10, SEQ ID No.11, SEQ ID No.12, AP, SEQ ID No.13, RER, PQ, GPR, SEQ ID No.14, SEQ ID No.15, SEQ ID No.16, VR, LN, SEQ ID No.18, SEQ ID No.19, SEQ ID No.20, SEQ ID No.21, SEQ ID No.22, FTE, SEQ ID No.23, SEQ ID No.24, SEQ ID No.25, SEQ ID No.26, SEQ ID No.27, SEQ ID No.28, LQ, SEQ ID No.29, NVG, SEQ ID No.30, PNH, PH, VL, LIE and TPT.

It was found in functional study on the active peptide, EGAR in the active peptide shows notable pairing with AMPR receptor, and can selectively inhibit AMPA receptor-mediated synaptic transmission of hippocampal neuron of mouse, and reduce postsynaptic current of hippocampal neuron, but not affect electrophysiological function of NMDA receptor in hippocampal neuron. Furthermore, it can inhibit excessive excitability of an overexcited neuron. In addition, in a mouse epilepsy model, epilepsy symptoms of an epileptic mouse stimulated by PTZ are relieved after EGAR treatment, which shows that EGAR has a significant antiepileptic effect.

In consideration of this, a third aspect of the present application provides a tetrapeptide for inhibiting an AMPA receptor and having an amino acid sequence of SEQ ID No.17.

A fourth aspect of the present application provides use of the above-mentioned active peptide in preparation of an antiepileptic food or drug.

A fifth aspect of the present application provides use of the above-mentioned tetrapeptide for inhibiting an AMPA receptor in preparation of an antiepileptic food or drug.

A sixth aspect of the present application provides a method for treating epilepsy, including administrating to an epileptic patient a drug containing a therapeutically effective amount of a tetrapeptide with an amino acid sequence of SEQ ID No.17.

DETAILED DESCRIPTION

Figure 1:
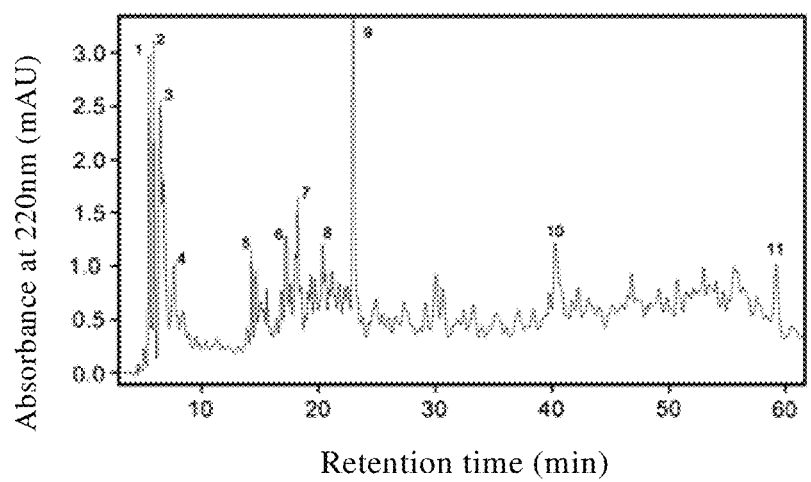
FIG. 1 is an RP-HPLC chromatogram of an active peptide prepared in Example 1.

To make objects, technical solutions and advantages of the present application more clear, technical solutions in examples of the present application will be clearly and completely described with reference to drawings and the examples of the present application. Obviously, the examples described are part of examples of the present application, rather than all examples. Based on the examples in the present application, all other examples obtained by those skilled in the art without creative work belong to the protection scope of the present application.

Raw materials used in each example of the present application and sources thereof are as follows: Neutral protease: from Novozymes biotechnology Co., Ltd;

TTX, PTX, CNQX, APV, NMDA, and AMPA: from TOCRIS Bioscience;

Papain, PTZ: From Sigma Aldrich; and

Synthetic EGAR: from Shanghai Qiang Yao Co., Ltd.

Example 1 Preparation of an Active Peptide

1. Preparation of the Active Peptide 5 kg of salmon skin is settled to a volume of 15 L by NaOH solution with a mass content of 0.2%, soaked for 12 h at normal temperature, and drained. The salmon skin is crushed, and beaten with deionized water that is 5 times salmon skin weight, and after pH is adjusted to 7.0, a slurry is obtained.

Neutral protease is added to the above slurry in an amount of 0.1% (i.e. 400 U/g salmon skin), and is subjected to enzymolysis for 5 hours at 50° C. Then papain is added to enzymatic hydrolysate in an amount of 0.2% (i.e. 400 U/g salmon skin), and the enzymolysis is continuously proceeded for 2 h at 60° C. After completion of the enzymolysis, enzyme inactivation is proceeded for 10 minutes at 100° C.

The enzymatic hydrolysate is centrifuged after the enzyme inactivation, and the centrifuged supernatant is subjected to membrane filtration by using a ceramic membrane (from Xiamen Starmen) with a pore diameter of 200 nm, clear liquid obtained after membrane filtration is concentrated to a concentration of 30 Baume by using R-151 concentrator (from BUCHI, Switzerland), then an activated carbon is added to the concentrated solution in an amount of 20%, to decolorize at 55° C. for 1 hour. After filtering to remove the activated carbon, the clear liquid is spray-dried, to obtain 620 g of active peptide.

2. Structural Identification of the Active Peptide

The active peptide prepared as above is diluted to a concentration of 2 mg/mL with deionized water, a gradient elution is performed using RP-HPLC (XBridge BEH130, 4.6*250 nm, Waters company, US). Elution conditions are as follows:

Mobile phase A: V(water):V(trifluoroacetic acid)=100:0.1;

Mobile phase B: V(acetonitrile):V(water):V(trifluoroacetic acid)=80:20:0.1;

Detection wavelength: UV220 nm;

Flow velocity: 0.6 mL/min;

Column temperature: 32° C.;

Injection volume: 50 µL;

Gradient program: 0-10 min, mobile phase B: 0%-5%; 10-20 min, mobile phase B: 5%-5%; 20-35 min, mobile phase B: 5%-9%; 35-45 min, mobile phase B: 9%-13%; 45-60 min, mobile phase B: 13%-13%; 60-70 min, mobile phase B: 13%-70%; and 70-90 min, mobile phase B: 70%-70%.

As shown in FIG. 1, there are 11 major absorption peaks appeared during the gradient elution of the active peptide prepared as above. Eluents corresponding to the 11 major absorption peaks are collected, and sequence of polypeptide in each component is analyzed by using Q-TOF2 mass spectrometer (Micromass, Britain). The results are shown in Table 1.

TABLE 1

| Polypeptide sequence in each component | |
|---|---|
| Component No. | Polypeptide sequence |
| 1 | WYN, SEQ ID No. 1, SEQ ID No. 2, SEQ ID No. 3 |
| 2 | SEQ ID No. 4, QK, SEQ ID No. 5, NK, NPR |
| 3 | TQ, RGF, SEQ ID No. 6, SR, SEQ ID No. 7 |
| 4 | SEQ ID No. 8, SEQ ID No. 9, GR, SSP, KR, AK, GGH, SEQ ID No. 10 |
| 5 | SEQ ID No. 11, SEQ ID No. 12, AP, SEQ ID No. 13, RER |
| 6 | PQ, GPR, SEQ ID No. 14, SEQ ID No. 15, SEQ ID No. 16, SEQ ID No. 17 |
| 7 | VR, LN, SEQ ID No. 18, SEQ ID No. 19, SEQ ID No. 20, SEQ ID No. 21 |
| 8 | SEQ ID No. 22, FTE, SEQ ID No. 23, SEQ ID No. 24, SEQ ID No. 25 |
| 9 | SEQ ID No. 26, SEQ ID No. 27, SEQ ID No. 28, LQ |
| 10 | SEQ ID No. 29, NVG, SEQ ID No. 30, PNH, PH |
| 11 | VL, LIE, TPT |

Example 2 Molecular Dynamic Simulation Test

AMBER11 simulation suite is used for molecular dynamic simulation and data analysis. Full atom point charge force field (AMBER FF03) shows a good balance between the results of α-helix and β-sheet and is used to describe a peptide. Aqueous solvent is expressly represented by TIP3P model. Parameters generated by EGAR are as follows: after geometry optimization, electrostatic potential of EGAR is obtained at HF/6-31G** level. Part of charges is derived from use of a restricted electrostatic potential (RESP) method to match gas phase electrostatic potential, and other mechanical parameters of EGAR molecule are taken from AMBER GAFF parameter set. The missing interaction parameters in the ligand are generated using antechamber tools in AMBER. The system is firstly minimized using steepest descent algorithm in 2000 steps, and then is subjected to MD simulation of 5 nanoseconds by using NPT entirety. Pressure is coupled to 1 bar with 1.0 ps anisotropic connection time, and the temperature during simulation is maintained at 300K with 0.1 PS coupling time. Long-range electrostatic is calculated with the particle mesh Ewald Method (PEM). SHAKE is used to limit a hydrogen atom-connecting bond, so that time step is 2.0 fs in simulation. Two fixed points, 0.8 nanometers and 1.2 nanometers, are used to evaluate non-bonded interaction respectively. Then, binding energy at 300K is estimated by using MM-GBSA. CPU of 192 AMD Opteron™ processor (2.0 GHz) is used for the above calculation.

Figure 2A:
FIG. 2A to FIG. 2D are computer simulation graphs of EGAR binding to an AMPA receptor.
Figure 2B:
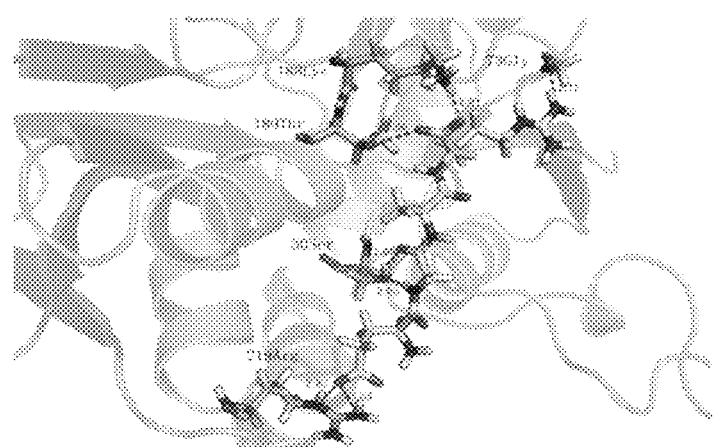
Figure 2C:
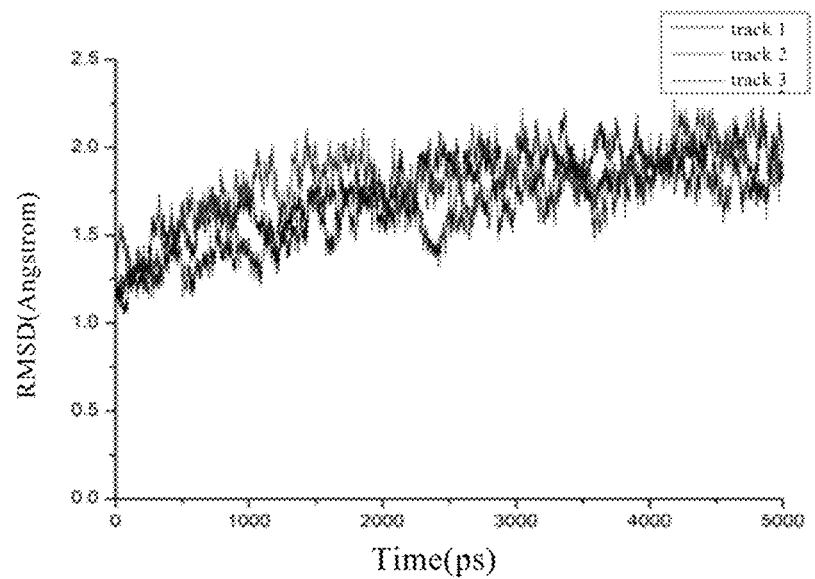
Figure 2D:
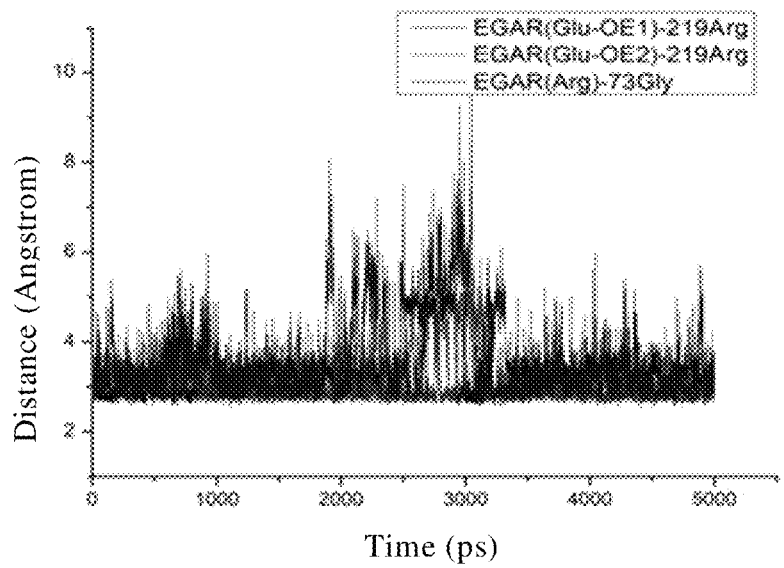

FIG. 2A to FIG. 2D are computer simulation graphs of EGAR binding to an AMPA receptor. Wherein, EGAR-AMPAR complex morphology in FIG. 2A shows that EGAR is bound to S1S2 domain of AMPAR; FIG. 2B shows that a hydrogen bond is formed between Arg219 and Gly73 residues of AMPAR and EGAR; FIG. 2C shows a distance between EGAR and AMPAR in 5000 ps simulation, and RMSD of AMPAR remains stable at about 1.75 angstroms in three repetitive simulations, which indicates the complex is relatively stable; FIG. 2D shows time dependence of distances of three strong hydrogen bonds between EGAR and AMPAR ((Glu-OE1) –219Arg, (Glu-OE2) –219Arg, Arg –73Gly), and distances between hydrogen donors and receptors are less than 3.5 angstroms.

The above results show: EGAR can stably bind to an AMPA receptor.

Example 3 Animal Experiment

This animal experiment protocol is approved by the animal care and use committee of Zhongshan University, and meets the experimental animal usage criteria of national health mechanism.

1. Reagents, Animals and Materials

ACSF: containing 124 mM sodium chloride, 2.5 mM potassium chloride, 2 mM calcium chloride, 2 mM magnesium chloride, 1.25 mM sodium dihydrogen phosphate, 26 mM sodium bicarbonate and 10 mM glucose; and saturated to pH 7.2-7.4 with 95% $O_2$/5% $CO_2$.

C57BL/6 mice: 2-3 weeks old, 15-20 grams, each captive in a cage at 20-22° C., free access to food and water, and kept in an environment of 12 hour light/dark cycle.

EGAR solution: a synthetic EGAR freeze-dried powder is dissolved in 115 µL of distilled water to be used as a stock solution, and during experiment the stock solution is diluted with the above AXSF to EGAR solutions with final concentrations of 100 µM, 50 µM, 20 µM, and 1 µM respectively for use.

Internal liquid: containing 140 mM potassium gluconate, 5 mM sodium chloride, 1 mM calcium chloride, 2 mM MgATP, 10 mM EGTA and 10 mM HEPES, pH 7.2-7.4, being subject to aseptic filtration before recording.

External liquid: containing 140 mM sodium chloride, 5 mM potassium chloride, 1.5 mM calcium chloride, 1 mM magnesium chloride, 10 mM HEPES and 10 mM glucose, pH 7.2-7.4; being subject to aseptic filtration before recording.

2. Preparation of Brain Tissue

Hippocampus is taken from a C57BL/6 mouse to do whole-cell recording. The mouse is deep narcotized with 20% urethane before being decollated, then its brain is rapidly removed and immersed in ice-cold ACSF, then the brain is trimmed, and fixed onto a vibration slicer (Leica VT1000A, Germany) to be cut into coronal slices of 350 microns. The slices are incubated with ACSF for at least 1 hour at room temperature before recording.

3. Electrophysiological Experiment

The slices of the hippocampus are transferred to an underwater recording room (Warner instrument). In the recording room, the slices are continuously perfused with ACSF at a speed of 3 ml/min, and whole-cell records of neurons of CA1 region of the hippocampus are performed by those experimenters who are not distinguished between a control group and a treated group. The neurons are identified through morphological recognition using an infrared ray differential interference phase-contrast microscope (BX51W, Olympus, Japan). A borosilicate microtube of 1.5 mm (external diameter)×0.86 mm (internal diameter) is drawn via a flame Brown electrode drawing instrument (P-97, Sutter instrument) using a 4 stage drawing scheme, to form a recording electrode with a resistance between 6-9 megohms. The recording electrode for recording is filled with above-mentioned internal liquid, and a whole-cell recording is proceeded by using above-mentioned external liquid.

Bipolar polytetrafluoroethylene insulated iridium is used to perform a voltage-clamp recording of excitatory postsynaptic currents (EPSCs), and platinum microelectrode (AM system) is induced at a frequency of 0.0167 Hz. Records are taken by a Multiclamp 700B amplifier, filtered at 10 kHz, sampled at 200 microseconds, and recorded to a personal computer by using pClamp10.2 software, and then analyzed by using Axon Digidata 1440A and pClamp10.2 (Molecular Devices).

Experiments mentioned below are carried out respectively, and the results are represented by an average value±S.E.M. In addition to data analysis of cumulative probability by the means of K-S test, statistical analyses of biological data are all performed by using T-test. All the statistical analyses are done by using SPSS 13.0 software.

(1) EPSCs of slices treated by EGAR are recorded, while EPSCs of slices without EGAR treatment is as contrast, and 10 μM of PTX is added into the external liquid to separate mEPSCs out.

Figure 3A:
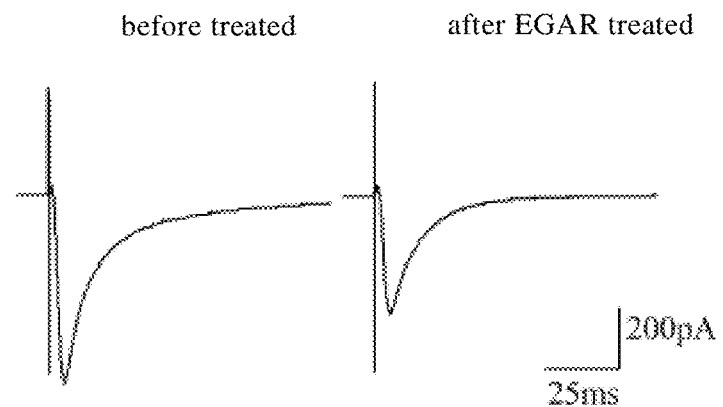
FIG. 3A to FIG. 3G are electrophysiological graphs of EPSC and mEPSC of mouse hippocampal slices.
Figure 3B:
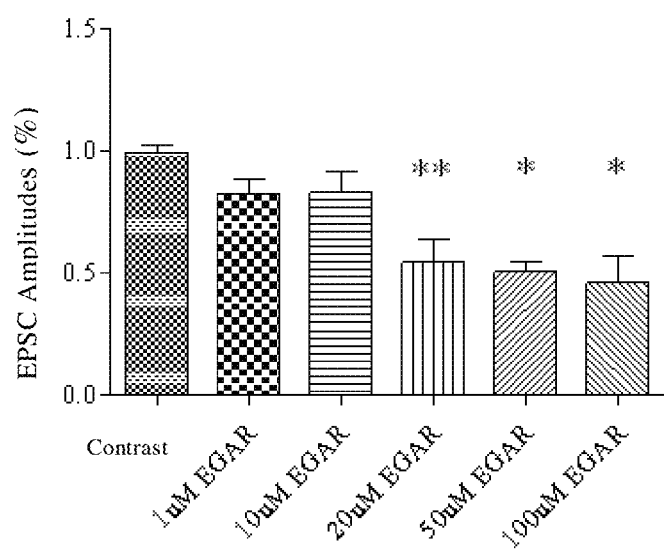
Figure 3C:
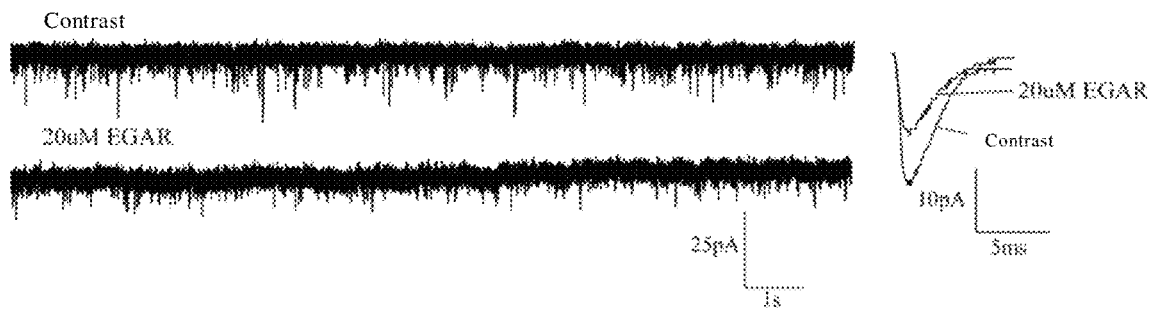
Figure 3D:
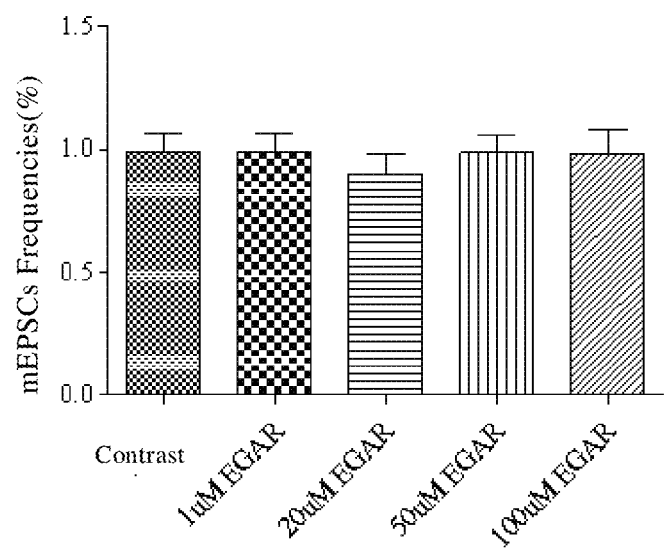
Figure 3E:
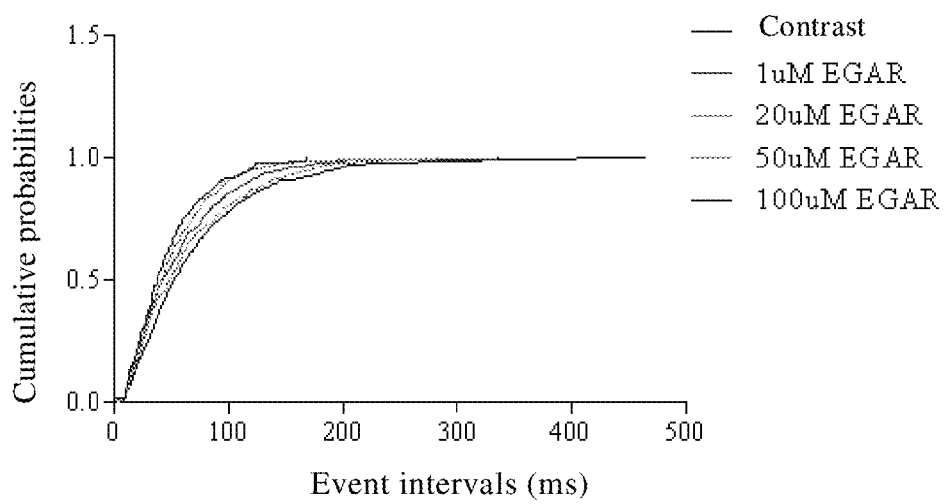
Figure 3F:
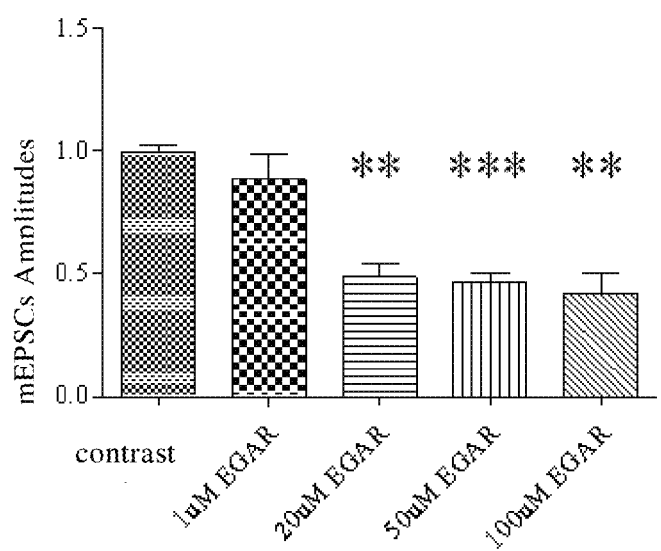
Figure 3G:
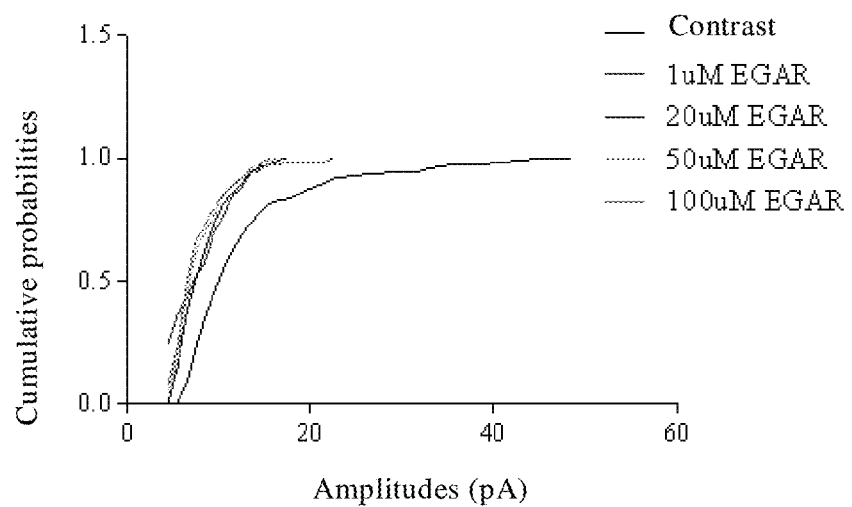

FIG. 3A to FIG. 3G are electrophysiological graphs of EPSC and mEPSC of mouse hippocampal slices. Wherein: FIG. 3A shows sample traces of EPSCs that are recorded from pyramidal cells of CA1 region before and after EGAR administration; bar charts of EPSC amplitudes in FIG. 3B show a significant difference between control group and EGAR treated groups at 20 μM ( P<0.03), 50 μM ( P<0.03) and 100 μM ( P<0.03); FIG. 3C is mEPSC records of pyramidal cells of CA1 region; histograms of FIG. 3D show that compared with the control group, the slices treated with EGAR has no change at mEPSC frequencies; cumulative probabilities of mEPSC event intervals in FIG. 3E show that there is no difference between a control group and EGAR treated groups at concentrations; bar charts of FIG. 3F show amplitudes of mEPSCs of EGAR treated groups at 20 μM ( P<0.03), 50 μM ( P<0.03) and 100 μM ( P<0.03) all reduce; cumulative probabilities of mEPSC amplitudes in FIG. 3G show an amplitude of EGAR treated groups at concentrations is reduced compared with a control group (K-S test, p<0.05).

The above results show: in isolated hippocampal slices experiment, a certain concentration of EGAR can inhibit excitatory postsynaptic current (EPSC) and micro excitatory postsynaptic current (mEPSC).

(2) after blocking components of NMDA receptor-mediated EPSCs by adding 50 μM of D-APV to ACSF and blocking AMPAR-mediated EPSCs by adding 10 μM of CNQX to ACSF, remaining EPSCs of both them are also recorded. 10 μM of PTX is added in external liquid to isolate mEPSCs. After 10 μM of CNQX and 20 μM of EGAR and also 50 μM of D-APV (an antagonist of NMDA receptor) and 20 μM of EGAR are added to ACSF, mEPSCs are also recorded. By adding 10 μM of CNQX or 50 μM of D-APV to ACSF, NMDAR-mediated or AMPAR-mediated mEPSCs are isolated.

Figure 4A:
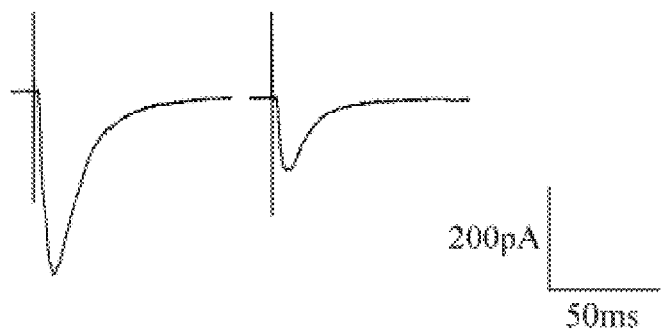
FIG. 4A to FIG. 4D are electrophysiological graphs of AMPAR-mediated EPSC of mouse hippocampal slices.
Figure 4B:
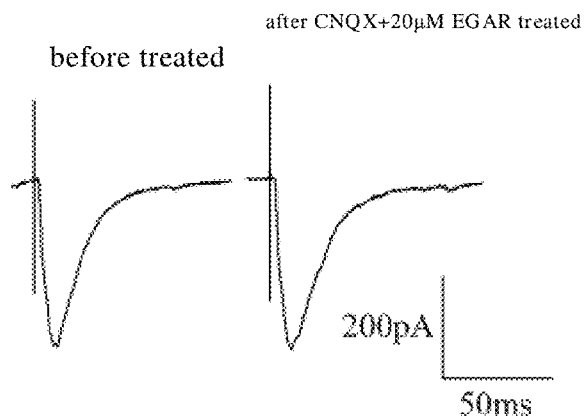
Figure 4C:
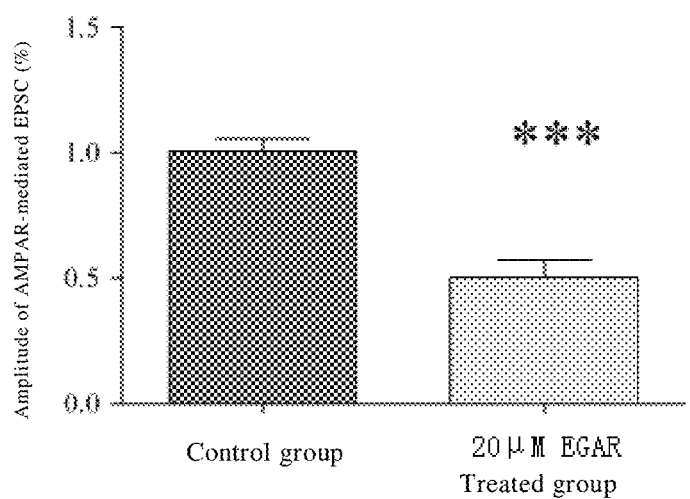
Figure 4D:
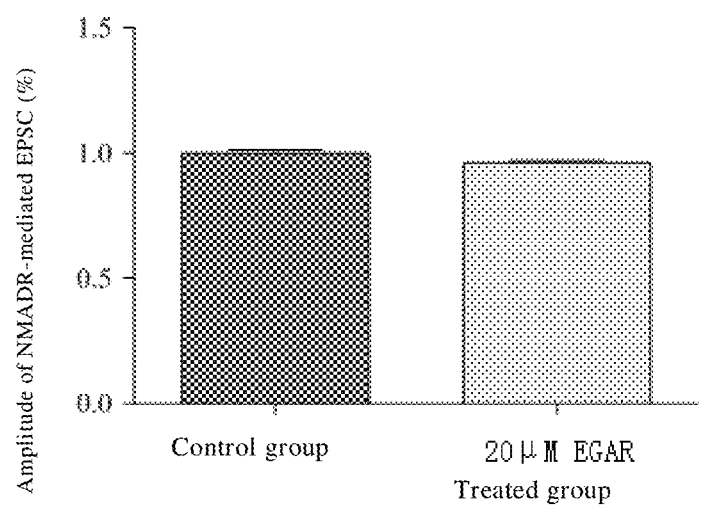

FIG. 4A to FIG. 4D are electrophysiological graphs of AMPAR-mediated EPSC of mouse hippocampal slices. Wherein: FIG. 4A shows representative tracks of hippocampal CA1 region treated with 50 μM of D-APV (an antagonist of NMDA receptor) before and after adding 20 μM of EGAR; FIG. 4B shows representative tracks of CA1 region of hippocampal slices treated with 10 μM of CNQX (a competitive antagonist of non-NMDA receptor) before and after adding 20 μM of EGAR; FIG. 4C is a bar chart showing that an amplitude of AMPAR-mediated EPSC of a treated group added with 50 μM of D-APV and 20 μM of EGAR is significantly lower compared with an amplitude of AMPAR-mediated EPSC of a control group (*** P<0.01, and in t test, n=6); FIG. 4D is a bar chart showing that an amplitude of NMADR-mediated EPSC of a treated group in which neurons are treated with 10 μM of CNQX and then 20 UM of EGAR is added is not changed compared with an amplitude of NMADR-mediated EPSC of a control group (P>0.05, t test, n=6).

The above results show: EGAR can selectively inhibit AMPAR-mediated excitatory postsynaptic current (EPSC).

(3) With regard to a NMDAR-mediated current record, 100 μM of NMDA is added into the above-mentioned external liquid; and with regard to an AMPAR-mediated current record, 20 μM of AMPA is added into above-mentioned external liquid.

Figure 5A:
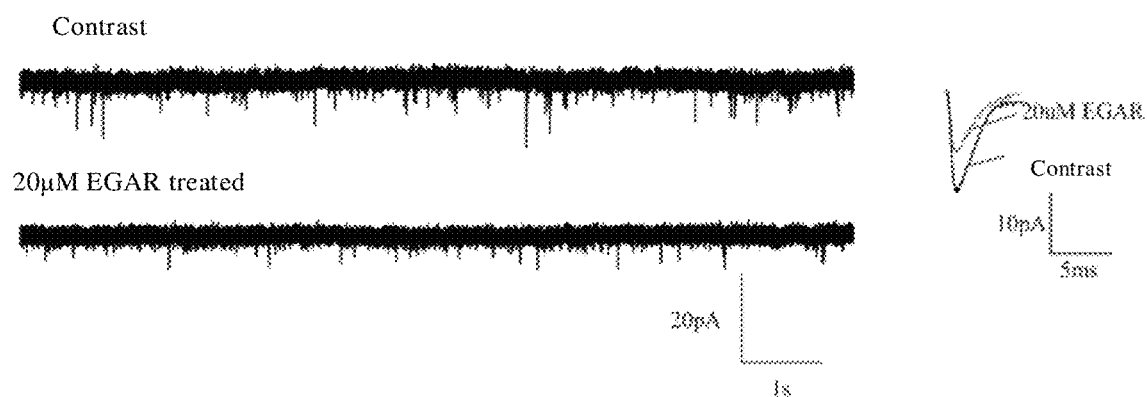
FIG. 5A to FIG. 5H are electrophysiological graphs of EGAR selectively inhibiting AMPAR-mediated mEPSC.
Figure 5B:
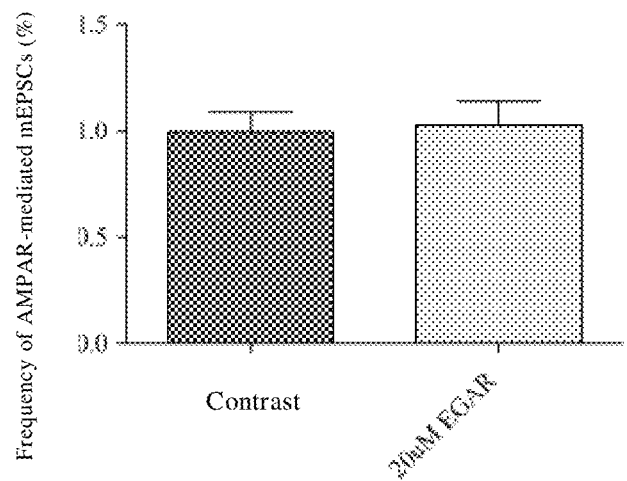
Figure 5C:
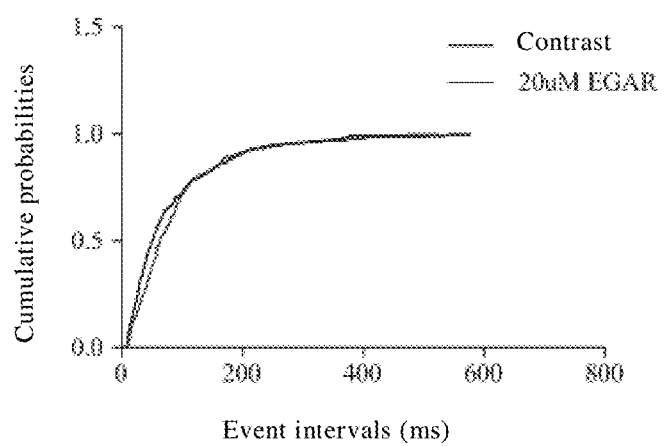
Figure 5D:
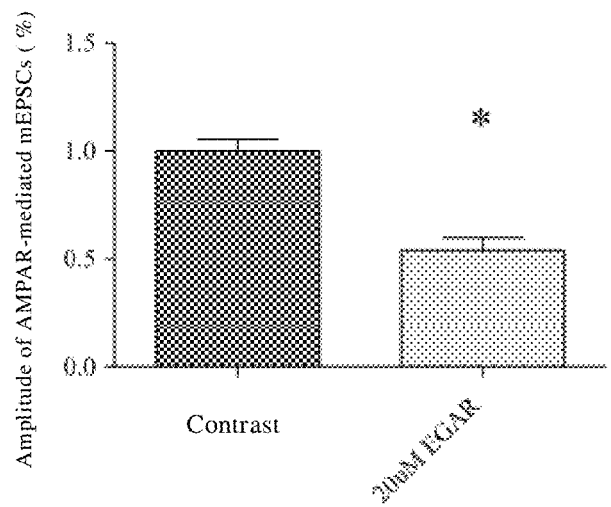
Figure 5E:
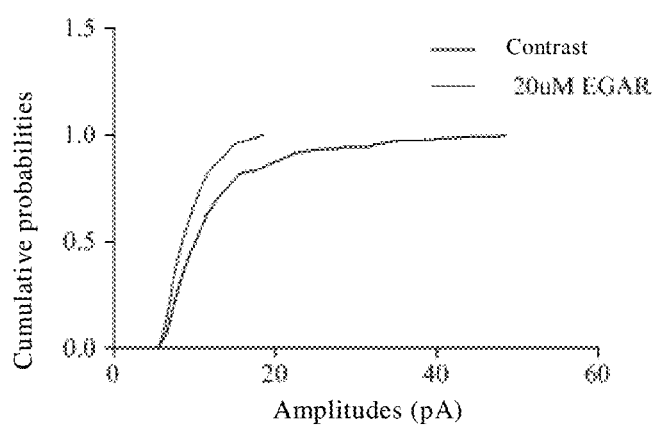
Figure 5F:
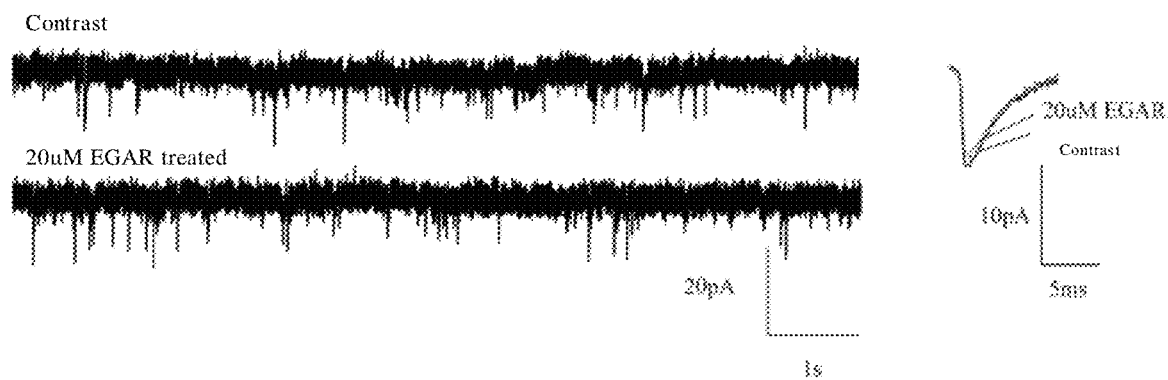
Figure 5G:
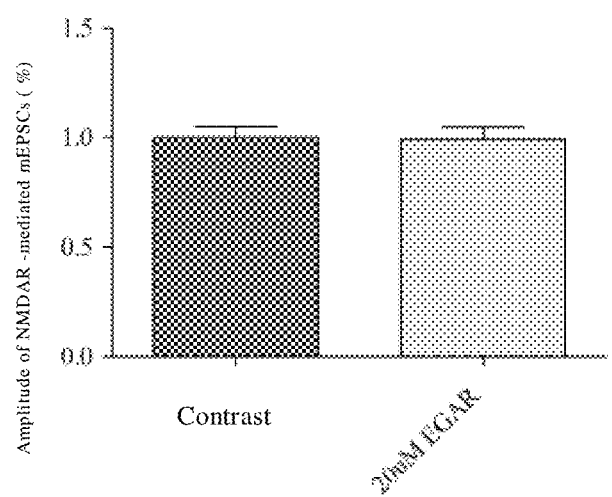
Figure 5H:
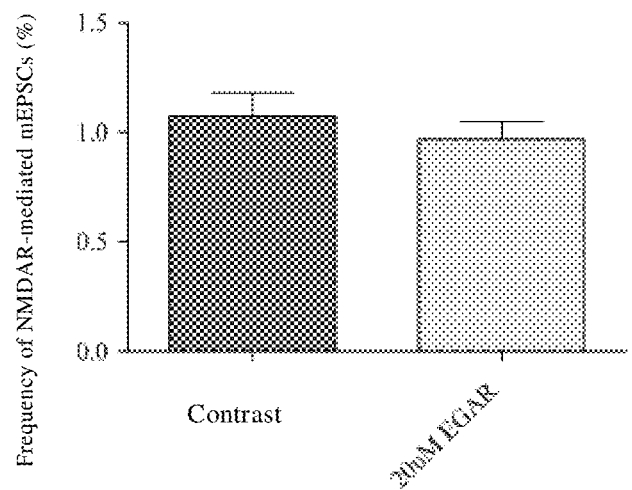

FIG. 5A to FIG. 5H are electrophysiological graphs of EGAR selectively inhibiting AMPAR-mediated mEPSC. Wherein: FIG. 5A shows sample traces of AMPAR-mediated mEPSCs of a control group and a EGAR treated group; FIG. 5B is a bar chart showing that compared with a control group, frequencies of AMPAR-mediated mEPSCs of neurons treated with EGAR do not change (P>0.05, t test, and N=6); cumulative probabilities of mEPSC event intervals in FIG. 5C show there is no difference in frequency between a control group and a EGAR treated group (K-S test, p>0.05, n=6); bar charts of FIG. 5D represent that according to records of neurons treated by EGAR, amplitude of AMPAR-mediated mEPSCs decline compared with a control group (* P<0.05, t test, n=6); cumulative probabilities of mEPSCs amplitudes of FIG. 5E show that compared with a control group, an amplitude of a EGAR treated group reduces (K-S test, p<0.05, n=6); FIG. 5F shows representative tracks of NMDA receptor-mediated mEPSCs of CA1 neurons treated with NMDA (100 μM) before and after adding EGAR (20 μM); FIG. 5G is a bar chart showing an quantization effect of an influence of 100 μM of NMDA plus 20 μM of EGAR on amplitudes of NMDAR-mediated mEPSCs, and the result shows that there is no significant difference between groups (P>0.05, t test, n=6); FIG. 5H is a bar chart showing an quantization effect of an influence of 100 μM of NMDA plus 20 μM of EGAR on frequencies of NMDAR-mediated mEPSCs, and the result shows that there is no significant difference between groups (P>0.05, t test, N=6).

The above results show: EGAR can selectively inhibit AMPA-mediated micro excitatory postsynaptic current (mEPSC).

(4) With regard to records of currents induced by NMDA, 100 μM of NMDA is added into above-mentioned external liquid; with regard to records of currents induced by AMPA, 20 μM of AMPA is added into above-mentioned external liquid.

Figure 6A:
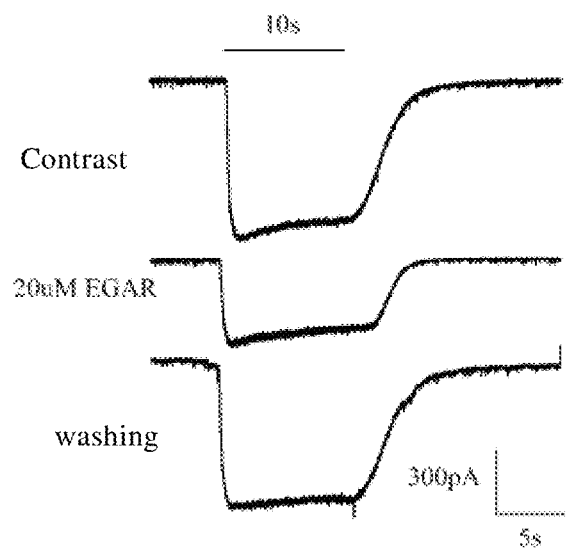
FIG. 6A to FIG. 6D are electrophysiological graphs of EGAR selectively inhibiting AMPA-induced currents.
Figure 6B:
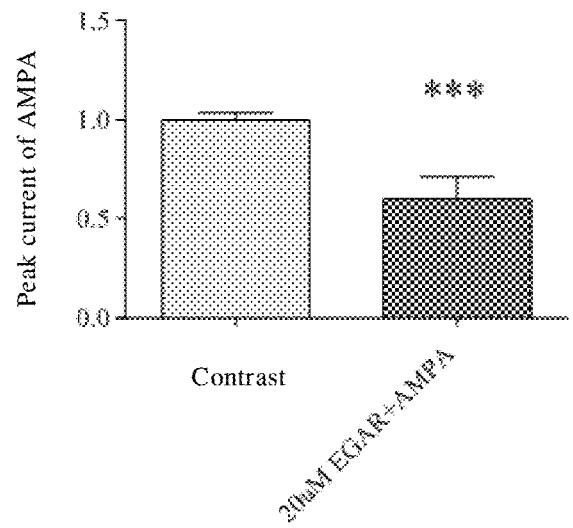
Figure 6C:
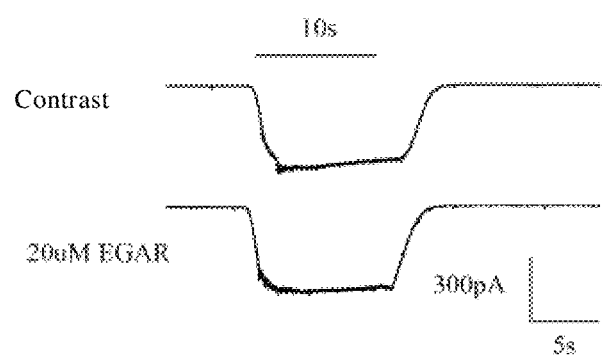
Figure 6D:
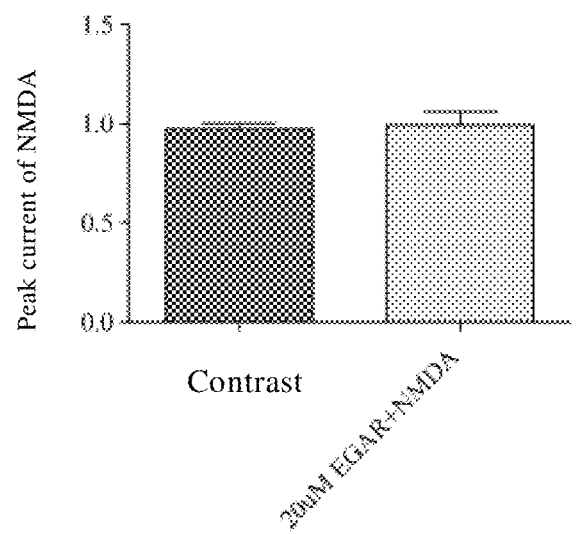

FIG. 6A to FIG. 6D are electrophysiological graphs of EGAR selectively inhibiting a current induced by AMPA. Wherein: FIG. 6A shows representative tracks of patch clamp experiments, which show an inward current induced by 20 μM of AMPA is reduced in the presence of EGAR, where the horizontal bar indicates application time of the used drug, the upper trace and the middle trace respectively indicate an AMPA processing and a co-processing of AMPA and 20 μM of EGAR, and the lower trace indicates the portion that AMPA is reacted returns to a control level after EGAR being washed away, and the cell is voltage-clamped at −70 mV; FIG. 6B is a bar chart showing an quantization effect of 20 μM of AMPA plus 20 μM of EGAR on a peak current of AMPA, and the result shows that there is a significant difference between groups (* $P<0.01$, in t test, n=6); FIG. 6C shows an effect of 20 μM of EGAR on a current induced by NMDA; FIG. 6**D is a bar chart showing a quantization effect of 100 μM of NMDA plus 20 μM of EGAR on a peak current of NMDA, and the result shows that there is no significant difference between groups (P>0.05, t test, n=6).

The above results show: EGAR can selectively inhibit a current induced by AMPA.

(5) In an experiment of nominal zero magnesium, magnesium ions are replaced by sodium ions with the same osmotic concentration.

Figure 7A:
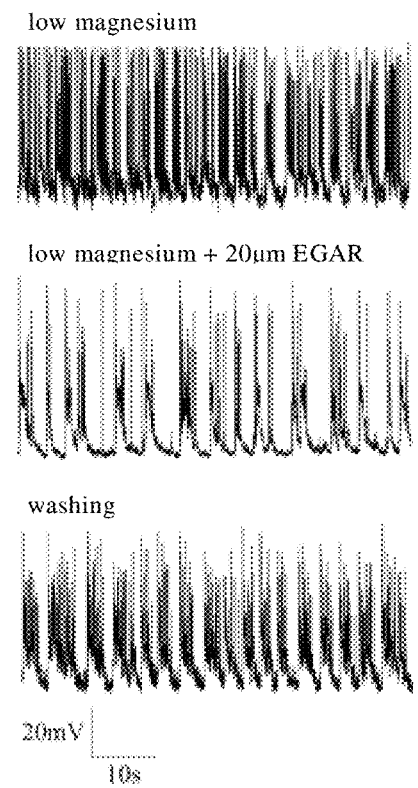
FIG. 7A and FIG. 7B are electrophysiological graphs of EGAR inhibiting epilepsy-like discharge of a hippocampal neuron induced by low magnesium external liquid.
Figure 7B:
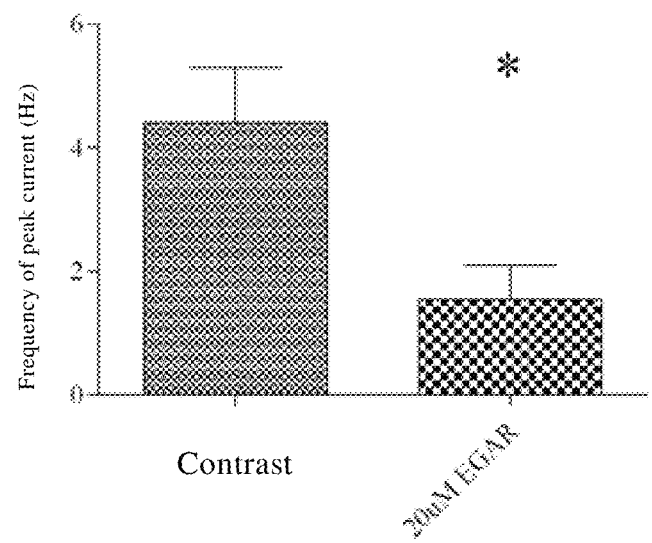

FIG. 7A and FIG. 7B are electrophysiological graphs of EGAR inhibiting epilepsy-like discharge of a hippocampal neuron induced by a low magnesium external liquid. Wherein: FIG. 7A shows peak currents induced by low magnesium under the condition of having and having no 20 μM of EGA treatment, and a trace of the sample recovered after washing; FIG. 7B is a bar chart showing an quantization effect of 20 μM of EGAR on a frequency of a peak current caused by low magnesium, and results show that there is a significant difference between groups (* $P<0.05$, t test, n=6).

The above results show: EGAR can inhibit epilepsy-like discharge of a hippocampal neuron inducted by a low magnesium external liquid.

(6) Effect of EGAR on electrophysiological properties of a neuron, and the results are shown in Table 2.

TABLE 2

Effect of EGAR on electrophysiological properties of a neuron

|  | Control group | 20 uM of EGAR treated group |
|---|---|---|
| Resting potential, mV | −68.57 ± 2.16 | −65.57 ± 1.23 |
| Input resistance, MΩ | 163.71 ± 7.29 | 164.57 ± 9.96 |
| Membrane capacitance, pF | 20.64 ± 0.79 | 19.07 ± 0.67 |
| Amplitude, mV | 89.43 ± 0.2 | 87.61 ± 1.18 |
| Action potential half width, ms | 0.95 ± 0.01 | 0.99 ± 0.01 |
| Frequency, Hz | 14.11 ± 3.84 | 13.53 ± 2.42 |
| Threshold potential, mV | −46.26 ± 0.5 | −45.61 ± 0.2 |

The results of table 2 show: EGAR has no significant effect on electrophysiological parameters of a CA1 neuron.

4. Model of PTZ-Induced Epilepsy Seizure

In order to determine anticonvulsive effect of EGAR, the degree of epilepsy after EGAR treatment is evaluated for the model of PTZ-induced epilepsy seizure. EGAR is injected into animals earlier 30 minutes than PTZ. The animals are randomly divided into 4 groups, and each group has 10 animals. 4 groups are given EGAR at 0, 1, 10 and 100 mg/kg respectively. All animals are intraperitoneally injected with PTZ at a dose of 55 mg/kg, and this dose can produce clonic seizures in all control animals.

Behaviors of mice are observed for 30 minutes immediately after PTZ injection. Two well-trained observers who do not know previous results analyze the behaviors of mice. Mice are placed in a transparent plastic cage, and are observed for 30 minutes. The cage is thoroughly cleaned by using wet/dry cloth and any olfactory clue is removed with 70% ethanol. Animals that show rampage and forelimb clonus or more serious behavior (rampage, clonus and fall down) are considered to be epilepsy in mouse brain edge. Epilepsy seizure is scored according to the following criteria: 0, no response; 1, immobile; 2, taste movement and grasping; 3, tremor; 4, head shaking; 5, rampage and forelimb clonus; 6, rampage, clonus and fall down; 7, death.

Figure 8A:
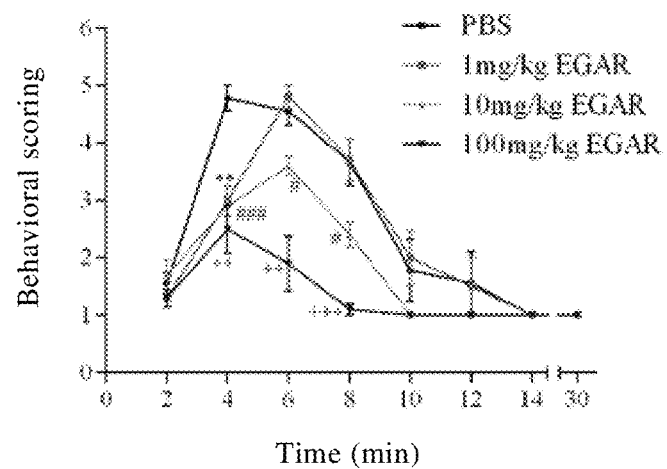
FIG. 8A and FIG. 8B show an effect of EGAR on PTZ-induced mouse epilepsy.
Figure 8B:
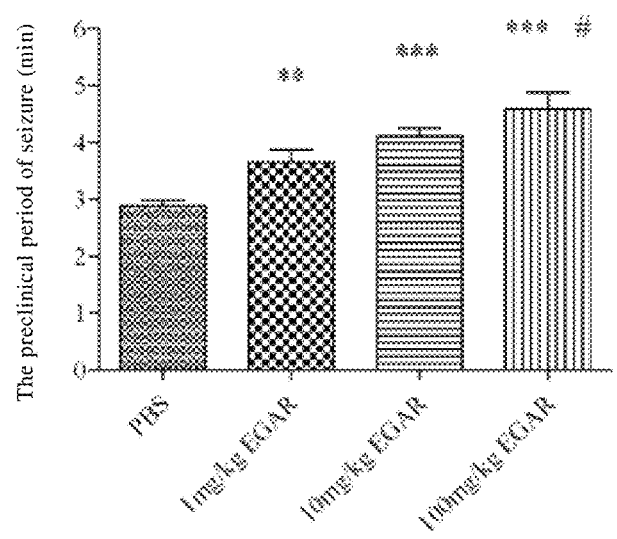

FIG. 8A and FIG. 8B show an effect of EGAR on PTZ-induced mouse epilepsy. Wherein: FIG. 8A shows behavior scores of 5 groups of mice treated with PBS, 1 mg/kg EGAR1, 10 mg/kg EGAR1 and 100 mg/kg EGAR1, respectively; FIG. 8B is a bar chart showing quantization effects of PBS, 1 mg/kg EGAR, 10 mg/kg EGAR and 100 mg/kg EGAR in a preclinical period of epilepsy seizure, the results show that there is a significant difference between PBS treated group and 1 mg/kg EGAR, 10 mg/kg EGAR and 100 mg/kg EGAR treated groups ( $P<0.03$,  $P<0.01$, # $p<0.05$, t test, n=6).

The above results show: in a behavioral experiment, EGAR can mitigate tic symptom of PTZ-inducted mouse epilepsy and extend the preclinical period of epilepsy seizure.

Finally it should be noted that: the above examples are merely illustrative of technical solutions of the present application, rather than to be limiting thereof; although the present application is described in detail with reference to foregoing examples, those skilled in the art shall understand: the technical solution described in foregoing examples can also be modified, or equivalently replaced with respect to part or all technical features therein; however, these modifications or replacements will not make essence of corresponding technical solutions depart from scope of the technical solutions of the examples of the present application.

What is claimed is:

1. A method for preparing an active peptide, comprising the following steps:
   1) soaking a salmon skin in an alkaline solution for 5-20 h and crushing, adding water and beating, and then adjusting the pH of the solution to 6.5-7.5, to obtain a slurry;
   2) subjecting the slurry to a first enzymolysis by using a neutral protease, to obtain a first enzymatic hydrolysate;
   3) subjecting the first enzymatic hydrolysate to a second enzymolysis by using papain enzyme and then inactivating the enzymes from the enzymolysis steps, to obtain a second enzymatic hydrolysate; and
   4) centrifuging the second enzymatic hydrolysate to obtain a centrifuged supernatant, and then subjecting the centrifuged supernatant to membrane filtration, concentration and decoloration, to prepare the active peptide;
   wherein the active peptide comprises a tetrapeptide with the amino-acid sequence of SEQ ID NO:17.

2. The method according to claim 1, wherein the alkaline solution is a 0.1-0.5% NaOH solution, and the mass/volume ratio of the salmon skin to the alkaline solution is from 1:(2-4).

3. The method according to claim 1, wherein the concentration of the neutral protease is 50-500 U/g, the concentration of the papain is 100-1000 U/g, and an amount ratio of the neutral protease to the papain is 1:(1-3).

4. The method according to claim 1, wherein the temperature of the first enzymolysis is from 30-60° C., the time of the first enzymolysis is 4-6 h, the temperature of the second enzymolysis is from 30-60° C., and the time of the second enzymolysis is 1-3 h.

5. The method according to claim 3, wherein the temperature of the first enzymolysis is from 30-60° C., the time of the first enzymolysis is 4-6 h, the temperature of the second enzymolysis is from 30-60° C., and the time of the second enzymolysis is 1-3 h.

6. The method according to claim 1, wherein the membrane filtration is with a ceramic membrane with a pore diameter of 50-1000 nm.

7. The method according to claim 1, further comprising: separating and purifying the active peptide by using reversed phase high performance liquid chromatography, to obtain the tetrapeptide with the amino acid sequence of SEQ ID NO:17.

* * * * *

SEQUENCE LISTING

<160> NUMBER OF SEQ ID NOS: 30

<210> SEQ ID NO 1
<211> LENGTH: 4
<212> TYPE: PRT
<213> ORGANISM: Salmo salar

<400> SEQUENCE: 1

Asn Thr Thr Met
1

<210> SEQ ID NO 2
<211> LENGTH: 6
<212> TYPE: PRT
<213> ORGANISM: Salmo salar

<400> SEQUENCE: 2

Asn Gly Gly Gly Gly Ser
1               5

<210> SEQ ID NO 3
<211> LENGTH: 4
<212> TYPE: PRT
<213> ORGANISM: Salmo salar

<400> SEQUENCE: 3

Pro Ala Leu His
1

<210> SEQ ID NO 4
<211> LENGTH: 4
<212> TYPE: PRT
<213> ORGANISM: Salmo salar

<400> SEQUENCE: 4

Ala Gly Gly Pro
1

<210> SEQ ID NO 5
<211> LENGTH: 4
<212> TYPE: PRT
<213> ORGANISM: Salmo salar

<400> SEQUENCE: 5

Met Ala Asp Thr
1

<210> SEQ ID NO 6
<211> LENGTH: 4
<212> TYPE: PRT
<213> ORGANISM: Salmo salar

<400> SEQUENCE: 6

Asn Ala Gly Lys
1

<210> SEQ ID NO 7
<211> LENGTH: 4
<212> TYPE: PRT
<213> ORGANISM: Salmo salar

<400> SEQUENCE: 7

Gln Gly Ala Lys
1

-continued

```
<210> SEQ ID NO 8
<211> LENGTH: 4
<212> TYPE: PRT
<213> ORGANISM: Salmo salar

<400> SEQUENCE: 8

Tyr Ser Ala Pro
1

<210> SEQ ID NO 9
<211> LENGTH: 4
<212> TYPE: PRT
<213> ORGANISM: Salmo salar

<400> SEQUENCE: 9

Asp Ala Gly Lys
1

<210> SEQ ID NO 10
<211> LENGTH: 5
<212> TYPE: PRT
<213> ORGANISM: Salmo salar

<400> SEQUENCE: 10

Asp Ser Gly Asp Gly
1               5

<210> SEQ ID NO 11
<211> LENGTH: 4
<212> TYPE: PRT
<213> ORGANISM: Salmo salar

<400> SEQUENCE: 11

Ala Gly Pro Ser
1

<210> SEQ ID NO 12
<211> LENGTH: 5
<212> TYPE: PRT
<213> ORGANISM: Salmo salar

<400> SEQUENCE: 12

Gly Ala Ala Gly Arg
1               5

<210> SEQ ID NO 13
<211> LENGTH: 4
<212> TYPE: PRT
<213> ORGANISM: Salmo salar

<400> SEQUENCE: 13

Val Asp Gly Lys
1

<210> SEQ ID NO 14
<211> LENGTH: 4
<212> TYPE: PRT
<213> ORGANISM: Salmo salar

<400> SEQUENCE: 14

Gly Pro Gln Gly
1

<210> SEQ ID NO 15
```

```
<211> LENGTH: 4
<212> TYPE: PRT
<213> ORGANISM: Salmo salar

<400> SEQUENCE: 15

Thr Gly Val Glu
1

<210> SEQ ID NO 16
<211> LENGTH: 5
<212> TYPE: PRT
<213> ORGANISM: Salmo salar

<400> SEQUENCE: 16

Ala Arg Gly Gly Lys
1               5

<210> SEQ ID NO 17
<211> LENGTH: 4
<212> TYPE: PRT
<213> ORGANISM: Salmo salar

<400> SEQUENCE: 17

Glu Gly Ala Arg
1

<210> SEQ ID NO 18
<211> LENGTH: 4
<212> TYPE: PRT
<213> ORGANISM: Salmo salar

<400> SEQUENCE: 18

Val Thr Gly Lys
1

<210> SEQ ID NO 19
<211> LENGTH: 5
<212> TYPE: PRT
<213> ORGANISM: Salmo salar

<400> SEQUENCE: 19

Gly His Ala Gly Glu
1               5

<210> SEQ ID NO 20
<211> LENGTH: 4
<212> TYPE: PRT
<213> ORGANISM: Salmo salar

<400> SEQUENCE: 20

Val Gly Gly Lys
1

<210> SEQ ID NO 21
<211> LENGTH: 4
<212> TYPE: PRT
<213> ORGANISM: Salmo salar

<400> SEQUENCE: 21

Gly His Gly Arg
1

<210> SEQ ID NO 22
<211> LENGTH: 5
<212> TYPE: PRT
```

```
<213> ORGANISM: Salmo salar

<400> SEQUENCE: 22

Ser Pro Gly Ala Gly
1               5

<210> SEQ ID NO 23
<211> LENGTH: 6
<212> TYPE: PRT
<213> ORGANISM: Salmo salar

<400> SEQUENCE: 23

Ala Gly Gly Pro Leu Gly
1               5

<210> SEQ ID NO 24
<211> LENGTH: 5
<212> TYPE: PRT
<213> ORGANISM: Salmo salar

<400> SEQUENCE: 24

Thr Gly Gly Pro Lys
1               5

<210> SEQ ID NO 25
<211> LENGTH: 6
<212> TYPE: PRT
<213> ORGANISM: Salmo salar

<400> SEQUENCE: 25

Gly Ala Gly Gly Met Thr
1               5

<210> SEQ ID NO 26
<211> LENGTH: 6
<212> TYPE: PRT
<213> ORGANISM: Salmo salar

<400> SEQUENCE: 26

Ala Ala Gly Pro Gly Leu
1               5

<210> SEQ ID NO 27
<211> LENGTH: 6
<212> TYPE: PRT
<213> ORGANISM: Salmo salar

<400> SEQUENCE: 27

Val Glu Lys Glu Lys His
1               5

<210> SEQ ID NO 28
<211> LENGTH: 4
<212> TYPE: PRT
<213> ORGANISM: Salmo salar

<400> SEQUENCE: 28

Thr Gly Pro Lys
1

<210> SEQ ID NO 29
<211> LENGTH: 4
<212> TYPE: PRT
<213> ORGANISM: Salmo salar
```

```
<400> SEQUENCE: 29

Ser Gly Gly Glu
1

<210> SEQ ID NO 30
<211> LENGTH: 4
<212> TYPE: PRT
<213> ORGANISM: Salmo salar

<400> SEQUENCE: 30

Gly Pro Ala Gly
1
```